United States Patent
Yamamoto et al.

(10) Patent No.: US 6,833,481 B2
(45) Date of Patent: Dec. 21, 2004

(54) PROCESS FOR PRODUCING 2-ALKYL-2CYCLOPENTENONES

(75) Inventors: Takeshi Yamamoto, Hiratsuka (JP); Kenichiro Adachi, Hiratsuka (JP); Shinya Watanabe, Hiratsuka (JP); Hideo Ujihara, Hiratsuka (JP); Toshimitsu Hagiwara, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/305,938

(22) Filed: Nov. 29, 2002

(65) Prior Publication Data

US 2003/0109755 A1 Jun. 12, 2003

(30) Foreign Application Priority Data

Nov. 30, 2001 (JP) .................................... P. 2001-366023

(51) Int. Cl.⁷ ............................................... C07C 45/00
(52) U.S. Cl. ........................ 568/341; 568/348; 568/364
(58) Field of Search ................................ 568/341, 348, 568/364

(56) References Cited

U.S. PATENT DOCUMENTS 4,310,701 A     1/1982     Wilson et al.

FOREIGN PATENT DOCUMENTS

| DE | 0154 604 | 4/1982 |
| EP | 0 033 604 A1 | 8/1981 |
| EP | 1 134 210 A1 | 9/2001 |
| JP | 51-23240 | 2/1976 |
| JP | 59-80625 | 5/1984 |
| JP | 59-29051 | 7/1984 |
| JP | 5-92934 | 4/1993 |
| JP | 58-42175 | 9/1993 |
| JP | 2000-327618 | 11/2000 |

OTHER PUBLICATIONS

XP–002169659 (1994)—Abstract.

*Primary Examiner*—Johann Richter
*Assistant Examiner*—Sikarl A. Witherspoon
(74) *Attorney, Agent, or Firm*—Sughrue Mion, PLLC

(57) ABSTRACT

Industrially advantageous processes for producing a 2-alkyl-2-cyclopentenone in high yields starting from a 2-(1-hydroxyalkyl)cyclopentanone or a 2-alkylidenecyclopentanone, which are obtainable from a cyclopentanone and a carbonyl compound. A 2-(1-hydroxyalkyl)cyclopentanone represented by the following general formula (1):

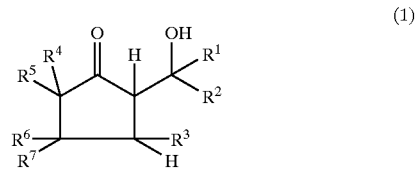

(1)

(wherein $R^1$, $R^2$, $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond) is subjected to dehydrative isomerization in the presence of a bromine compound and/or an iodine compound.

5 Claims, No Drawings

PROCESS FOR PRODUCING 2-ALKYL-2CYCLOPENTENONES

FIELD OF THE INVENTION

The present invention relates to processes for producing 2-alkyl-2-cyclopentenones useful as industrial products in organic synthetic chemistry, such as medicaments and flavor and fragrance raw materials, and also intermediates thereof.

BACKGROUND OF THE INVENTION

Heretofore, 2-alkyl-2-cyclopentenones represented by the general formula (2) are known as fruity and floral synthetic fragrance raw materials including jasmine as a representative. In particular, 2-amyl-2-cyclopentenone has a jasmine-like fruity and floral odor and is useful as a fragrance raw material [e.g., Gosei Koryo (Synthetic Flavor and Fragrance Raw Materials)-Kagaku to Shohin Chishiki (Chemistry and Knowledge on Commercial Products)—(written by Motoichi Indo, Kagaku Kogyo Nippo) p. 353].

Moreover, 2-alkyl-2-cyclopentenones are important as synthetic intermediates. For example, as described in Gosei Koryo (Synthetic Flavor and Fragrance Raw Materials)—Kagaku to Shohin Chishiki (Chemistry and Knowledge on Commercial Products)—(written by Motoichi Indo, Kagaku Kogyo Nippo) pp. 843–847, methyl jasmonate and methyl dihydrojasmonate are obtained by adding methyl malonate to 2-cis-pentenyl- and 2-pentyl-2-cyclopentenone and then subjecting the addition products to decarboxylation, respectively. These jasmonates are useful as flavor and fragrance raw materials having a jasmine-like floral odor.

Furthermore, 2-alkylcyclopentanones obtainable by hydrogenating the double bond of 2-alkyl-2-cyclopentenones are useful as flavor and fragrance raw materials. For example, it is described in Gosei Koryo (Synthetic Flavor and Fragrance Raw Materials)-Kagaku to Shohin Chishiki (Chemistry and Knowledge on Commercial Products)—(written by Motoichi Indo, Kagaku Kogyo Nippo) pp. 353–358 that 2-pentylcyclopentanone, 2-hexylcyclopentanone and 2-heptylcyclopentanone are useful as jasmine-like fruity and floral synthetic flavor and fragrance raw materials.

In addition, δ-lactones obtainable by oxidizing 2-alkylcyclopentanones, for example, using peracetic acid are useful as flavor and fragrance raw materials [Gosei Koryo (Synthetic Flavor and Fragrance Raw Materials)-Kagaku to Shohin Chishiki (Chemistry and Knowledge on Commercial Products)—(written by Motoichi Indo, Kagaku Kogyo Nippo) pp. 562–568].

Heretofore, as a process for producing a 2-alkyl-2-cyclopentenone represented by the formula (2), a process represented by the following reaction scheme (1) has been widely used.

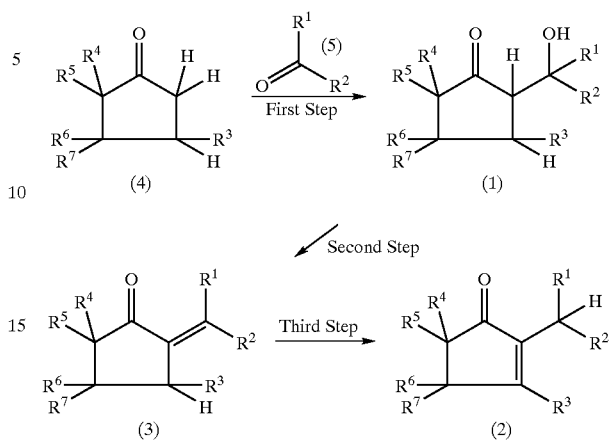

Reaction scheme (1)

The process involves the following three steps:

First step: a step of obtaining a 2-(1-hydroxyalkyl)cyclopentanone represented by the general formula (1) by treating a cyclopentanone represented by the general formula (4) with an aliphatic carbonyl compound represented by the general formula (5);

Second step: a step of obtaining a 2-alkylidenecyclopentanone represented by the general formula (3) by dehydrating a 2-(1-hydroxyalkyl)cyclopentanone represented by the general formula (1); and Third step: a step of producing a 2-alkyl-2-cyclopentenone represented by the general formula (2) by isomerizing a 2-alkylidenecyclopentanone represented by the general formula (3).

Of these steps, the first step is an application of the reaction, so-called aldol reaction which is well known and, in the case of existing no particular hindrance such as steric hindrance, a 2-(1-hydroxyalkyl)cyclopentanone is obtained in good yields under relatively mild conditions. Moreover, a process is also known wherein a 2-(1-hydroxyalkyl)cyclopentanone, a product in the first step is simultaneously dehydrated to afford a 2-alkylidenecyclopentanone in only one step. In this case, the reaction is particularly called as aldol condensation reaction.

However, there is room for improvement in the above production of a 2-alkyl-2-cyclopentenone via the above reaction or aldol condensation in view of the yields and operational methods and hence the process is by no means industrially advantageous.

For example, as shown in the following reaction scheme (2), U.S. Pat. No. 4,310,701 discloses a process for obtaining a 2-alkyl-2-cyclopentenone (9) by dehydrating an aldol (7) obtainable from the aldol reaction of cyclopentanone (6) with an aliphatic aldehyde using oxalic acid as a catalyst to afford a 2-alkylidenecyclopentanone (8) and heating it together with an n-butanol solution of concentrated hydrochloric acid to isomerize the double bond.

Reaction scheme (2)

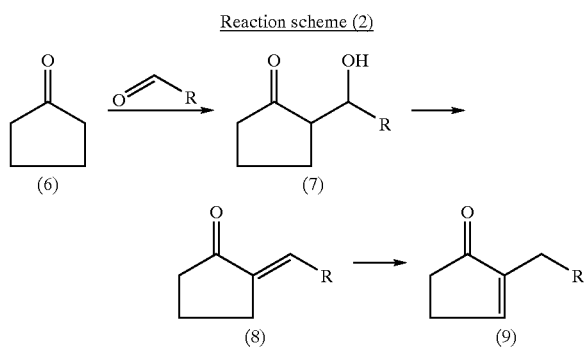

However, in this process, the yield of the compound (9) calculated based on the compound (6) is not so high and hence the process is not satisfactory. Moreover, some problems, e.g., the inevitable use of a large excess of n-butanol and a large amount of concentrated hydrochloric acid in the isomerization reaction from the compound (8) to the compound (9), are pointed out in view of the production efficiency and thus there is room for improvement as an industrial production process.

Furthermore, JP-A-5-92934 discloses a process for synthesizing a 2-alkyl-2-cyclopentenone (9) by subjecting the aldol (7) to dehydration and isomerization simultaneously in concentrated hydrochloric acid-n-butanol. However, even in this process, the yield of the compound (9) is not satisfactory and productivity is poor because of the use of a large excess of n-butanol and a large amount of concentrated hydrochloric acid. Thus, for the practical use, there is room for improvement.

Additionally, as a catalyst for the reaction of isomerizing the 2-alkylidenecyclopentanone (8) to the 2-alkyl-2-cyclopentenone (9), transition metal complex catalysts are known (JP-B-58-42175 and JP-B-59-29051). However, this process has problems that it produces relatively a large amount of by-products and these catalysts are expensive, so that it is desired to develop an isomerization catalyst which is inexpensive and also excellent in selectivity.

Moreover, as disclosed in JP-A-2000-327618, JP-A-59-80625 and JP-A-51-23240, isomerization processes using a hydrogen halide or a sulfonic acid are also known. However, in these cases, a large amount of a solvent is used and there is room for improvement of the yield, so that the processes are not industrially advantageous.

SUMMARY OF THE INVENTION

An object of the invention is to provide industrially advantageous production processes including production of a 2-alkyl-2-cyclopentenone in high yields using a 2-(1-hydroxyalkyl)cyclopentanone or a 2-alkylidenecyclopentanone, which are obtainable from a cyclopentanone and a carbonyl compound.

As a result of intensive studies in consideration of the above circumstances, the present inventors have found that dehydration and isomerization occur simultaneously in high selectivity by reacting a 2-(1-hydroxyalkyl)cyclopentanone represented by the general formula (1) in the presence of a bromine compound and/or an iodine compound as shown in the following reaction scheme (3), and thereby a 2-alkyl-2-cyclopentenone represented by the general formula (2) is obtained in high yields.

Reaction scheme (3)

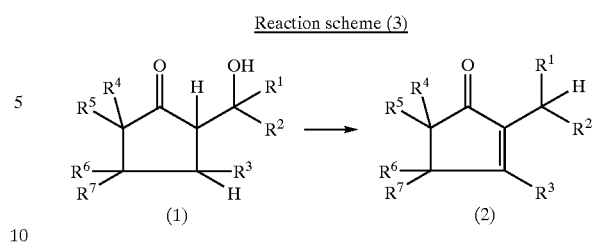

Furthermore, as shown in the following reaction scheme (4), they have found that the exocyclic double bond is selectively isomerized to endcyclic double bond by reacting a 2-alkylidenecyclopentanone represented by the following formula (3) in the presence of a catalytic amount of a bromine compound and/or an iodine compound, and thereby a 2-alkyl-2-cyclopentenone represented by the general formula (2) is obtained in high yields.

Reaction scheme (4)

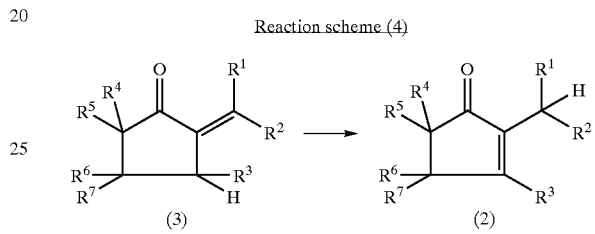

They have accomplished the invention as a result of further more studies.

That is, the invention relates to the following.

1) A process for producing a 2-alkyl-2-cyclopentenone represented by the following general formula (2):

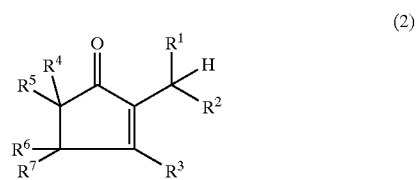

(2)

(wherein $R^1$, $R^2$, $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond), which comprises a step of dehydrative isomerization of a 2-(1-hydroxyalkyl)cyclopentanone represented by the following general formula (1):

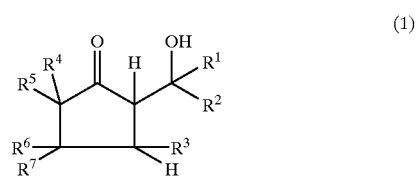

(1)

(wherein $R^1$, $R^2$, $R^3$, $R^4$, $R^5$, $R^6$ and $R^7$ are the same as above) in the presence of a bromine compound and/or an iodine compound.

2) A process for producing a 2-alkyl-2-cyclopentenone represented by the above general formula (2), which comprises a step of isomerization of a 2-alkylidenecyclopentanone represented by the following general formula (3):

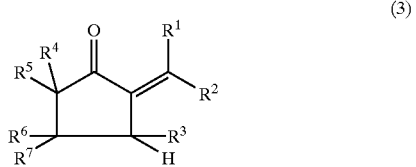

(wherein $R^1$, $R^2$, $R^3$, $R^4$, $R^5$, $R^6$ and $R^7$ are the same as above) in the presence of a bromine compound and/or an iodine compound.

DETAILED DESCRIPTION OF THE INVENTION

The following will explain the invention in further detail.

When the phrase "which may have one or more substituents" is used in this specification, the number of the substituents is not particularly limited and is preferably from 1 to 3.

First, there is explained a process for producing a 2-(1-hydroxyalkyl)cyclopentanone represented by the above general formula (1), which is used in the invention.

The production process is not particularly limited but, as a representative process, the compound can be produced by applying a well-known aldol reaction starting from a cyclopentanone represented by the following general formula (4)

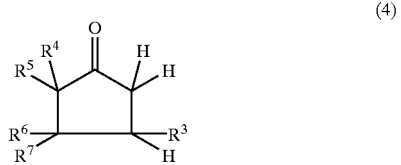

(wherein $R^3$ to $R^7$ are the same as above)
and a carbonyl compound represented by the following general formula (5)

(wherein $R^1$ and $R^2$ are the same as above).

An aldol reaction is described in Organic Reactions Vol. 16 (John Wiley & Sons INC., 1968), for example.

In the cyclopentanone represented by the above general formula (4), $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond.

As the substituent by which an alkyl group is substituted, an alkyl group having 1 to 3 carbon atoms may be mentioned, and as the substituent by which an aromatic group is substituted, an alkyl group having 1 to 3 carbon atoms may be mentioned.

Moreover, the ring which may have a double bond and formed by combining together each of (1) $R^6$ or $R^7$ with $R^3$ and (2) $R^6$ or $R^7$ with $R^4$ or $R^5$ includes hexahydroindanone, androstane-mono-one, androstene-mono-one, and the like.

Specific examples of the cyclopentanone represented by the above general formula (4) include cyclopentanone, 2-methylcyclopentanone, 3-methylcyclopentanone, 2-ethylcyclopentanone, 2-propylcyclopentanone, 2-isopropylcyclopentanone, 2-butylcyclopentanone, 2-tert-butylcyclopentanone, 2-iso-butylcyclopentanone, 2-pentylcyclopentanone, 2-hexylcyclopentanone, 2-heptylcyclopentanone, 2-octylcyclopentanone, 2-decylcyclopentanone, 2,2-dimethylcyclopentanone, 2,3-dimethylcyclopentanone, 2,4-dimethylcyclopentanone, and 2,3,4-trimethylcyclopentanone. Among them, preferred is cyclopentanone.

In the carbonyl compound represented by the above general formula (5), $R^1$ and $R^2$ each independently represents hydrogen atom, an alkyl group having 1 to 10 carbon atoms which may have one or more substituents or an aromatic group which may have one or more substituents, and $R^1$ and $R^2$ may be together combined to form a ring.

Specific examples of the carbonyl compound represented by the above general formula (5) include formalin, acetaldehyde, propanal, butanal, pentanal, 3-pentenal, 3-pentynal, hexanal, heptanal, octanal, nonanal, decanal, 2-methylpropanal, 2-methylbutanal, 2-methylpentanal, 2-methylhexanal, 2-methylheptanal, 2-methyloctanal, 3-methylbutanal, 3-methylpentanal, 3-methylhexanal, 4-methylpentanal, 5-methylhexanal, acetone, 2-butanone, 2-pentanone, 2-hexanone, 2-heptanone, 2-octanone, 2-nonanone, 4-methyl-2-pentanone, 3-pentanone, cyclopentanone, cyclohexanone and benzaldehyde.

Among the aliphatic carbonyl compounds represented by the above general formula (5), more preferred are compounds wherein $R^1$ is hydrogen atom and $R^2$ is an alkyl group having 1 to 10 carbon atoms which may have any one or more substituents or an aromatic group which may have any one or more substituents.

Specific examples of the compounds include acetaldehyde, propanal, butanal, pentanal, 3-pentenal, 3-pentynal, hexanal, heptanal, octanal, nonanal, decanal, 2-methylpropanal, 2-methylbutanal, 2-methylpentanal, 2-methylhexanal, 2-methylheptanal, 2-methyloctanal, 3-methylbutanal, 3-methylpentanal, 3-methylhexanal, 4-methylpentanal and 5-methylhexanal.

Further preferred aliphatic carbonyl compound represented by the above general formula (5) are compounds wherein $R^1$ is hydrogen atom and $R^2$ is a linear or branched alkyl group having 2 to 8 carbon atoms which may have one or more unsaturated bonds.

The reaction conditions for the reaction are not particularly limited but aimed 2-(1-hydroxyalkyl)cyclopentanone can be produced easily in high yields, for example, by the reaction using sodium hydroxide as a catalyst.

In the production of a compound represented by the general formula (2) using a 2-(1-hydroxyalkyl) cyclopentanone represented by the general formula (1) thus obtained, the above reaction product can be used as it is without purification or as a product purified by distillation or the like.

The following will explain the 2-(1-hydroxyalkyl) cyclopentanone represented by the following general formula (1):

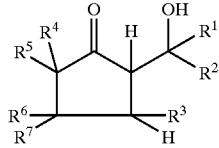

(1)

which is used in the invention. In the compound, $R^1$, $R^2$, $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond.

Examples of 1-hydroxyalkyl group to be bonded to the 2-position of the above cyclopentanone include hydroxymethyl group, 1-hydroxyethyl group, 1-hydroxypropyl group, 1-hydroxybutyl group, 1-hydroxypentyl group, 1-hydroxy-3-pentenyl group, 1-hydroxy-3-pentynyl group, 1-hydroxyhexyl group, 1-hydroxyheptyl group, 1-hydroxyoctyl group, 1-hydroxynonyl group, 1-hydroxydecyl group, 1-hydroxy-2-methylpropyl group, 1-hydroxy-2-methylbutyl group, 1-hydroxy-2-methylpentyl group, 1-hydroxy-2-methylhexyl group, 1-hydroxy-2-methylheptyl group, 1-hydroxy-2-methyloctyl group, 1-hydroxy-3-methylbutyl group, 1-hydroxy-3-methylpentyl group, 1-hydroxy-3-methylhexyl group, 1-hydroxy-4-methylpentyl group, 1-hydroxy-5-methylhexyl group, 1-hydroxy-1-methylethyl group, 1-hydroxy-1-methylpropyl group, 1-hydroxy-1-methylbutyl group, 1-hydroxy-1-methylpentyl group, 1-hydroxy-1-methylhexyl group, 1-hydroxy-1-methylheptyl group, 1-hydroxy-1-methyloctyl group, 1-hydroxy-1,3-dimethylbutyl group, 1-hydroxy-1-ethylpropyl group, 1-hydroxycyclopentyl group, 1-hydroxycyclohexyl group and hydroxyphenylmethyl group.

Moreover, as cyclopentanones substituted at the 2-position, there may be mentioned those wherein the following cyclopentanones are substituted by any of the above 1-hydroxyalkyl group at the 2-position. Specific examples of the cyclopentanones to be substituted by the above 1-hydroxyalkyl group include cyclopentanone, 5-methylcyclopentanone, 3- or 4-methylcyclopentanone, 5-ethylcyclopentanone, 5-propylcyclopentanone, 5-isopropylcyclopentanone, 5-butylcyclopentanone, 5-tert-butylcyclopentanone, 5-iso-butylcyclopentanone, 5-pentylcyclopentanone, 5-hexylcyclopentanone, 5-heptylcyclopentanone, 5-octylcyclopentanone, 5-decylcyclopentanone, 5,5-dimethylcyclopentanone, 4,5-dimethylcyclopentanone, 3,5-dimethylcyclopentanone, and 3,4,5-trimethylcyclopentanone.

Among the cyclopentanones substituted at the 2-position, preferred are compounds wherein $R^1$ is hydrogen atom, $R^2$, $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond.

More specifically, examples of 1-hydroxyalkyl group to be bonded to the cyclopentanones include hydroxymethyl group, 1-hydroxyethyl group, 1-hydroxypropyl group, 1-hydroxybutyl group, 1-hydroxypentyl group, 1-hydroxy-3-pentenyl group, 1-hydroxy-3-pentynyl group, 1-hydroxyhexyl group, 1-hydroxyheptyl group, 1-hydroxyoctyl group, 1-hydroxynonyl group, 1-hydroxydecyl group, 1-hydroxy-2-methylpropyl group, 1-hydroxy-2-methylbutyl group, 1-hydroxy-2-methylpentyl group, 1-hydroxy-2-methylhexyl group, 1-hydroxy-2-methyloctyl group, 1-hydroxy-3-methylbutyl group, 1-hydroxy-3-methylpentyl group, 1-hydroxy-3-methylhexyl group, 1-hydroxy-4-methylpentyl group and 1-hydroxy-5-methylhexyl group.

Moreover, as cyclopentanones substituted at the 2-position, there may be mentioned those wherein the following cyclopentanones are substituted by any of the above 1-hydroxyalkyl group at the 2-position. Specific examples of the cyclopentanones to be substituted by the above 1-hydroxyalkyl group include cyclopentanone, 5-methylcyclopentanone, 3- or 4-methylcyclopentanone, 5-ethylcyclopentanone, 5-propylcyclopentanone, 5-isopropylcyclopentanone, 5-butylcyclopentanone, 5-tert-butylcyclopentanone, 5-iso-butylcyclopentanone, 5-pentylcyclopentanone, 5-hexylcyclopentanone, 5-heptylcyclopentanone, 5-octylcyclopentanone, 5-decylcyclopentanone, 5,5-dimethylcyclopentanone, 4,5-dimethylcyclopentanone, 3,5-dimethylcyclopentanone, and 3,4,5-trimethylcyclopentanone.

Among the cyclopentanones substituted at the 2-position, more preferred are compounds wherein $R^2$ is an alkyl group having 1 to 10 carbon atoms which may have any one or more substituents or an aromatic group which may have any one or more substituents, and $R^1$, $R^3$, $R^4$, $R^5$, $R^6$ and $R^7$ each is hydrogen atom.

Specific examples of the preferred compounds include 2-(1-hydroxyethyl)cyclopentanone, 2-(1-hydroxypropyl)cyclopentanone, 2-(1-hydroxybutyl)cyclopentanone, 2-(1-hydroxypentyl)cyclopentanone, 2-(1-hydroxy-3-pentenyl)cyclopentanone, 2-(1-hydroxy-3-pentynyl)cyclopentanone, 2-(1-hydroxyhexyl)cyclopentanone, 2-(1-hydroxyoctyl)cyclopentanone, 2-(1-hydroxynonyl)cyclopentanone, 2-(1-hydroxydecyl)cyclopentanone, 2-(1-hydroxy-2-methylpropyl)cyclopentanone, 2-(1-hydroxy-2-methylbutyl)cyclopentanone, 2-(1-hydroxy-2-methylpentyl)cyclopentanone, 2-(1-hydroxy-2-methylhexyl)cyclopentanone, 2-(1-hydroxy-2-methylheptyl)cyclopentanone, 2-(1-hydroxy-2-methyloctyl)cyclopentanone, 2-(1-hydroxy-3-methylbutyl)cyclopentanone, 2-(1-hydroxy-3-methylpentyl)cyclopentanone, 2-(1-hydroxy-3-methylhexyl)cyclopentanone, 2-(1-hydroxy-4-methylpentyl)cyclopentanone and 2-(1-hydroxy-5-methylhexyl)cyclopentanone.

More preferred are compounds wherein $R^2$ is a linear or branched alkyl group having 2 to 8 carbon atoms which may have one or more unsaturated bonds, and $R^1$, $R^3$, $R^4$, $R^5$, $R^6$ and $R^7$ each is hydrogen atom.

Specific examples of the compounds include 2-(1-hydroxypropyl)cyclopentanone, 2-(1-hydroxybutyl)cyclopentanone, 2-(1-hydroxypentyl)cyclopentanone, 2-(1-hydroxy-3-pentenyl)cyclopentanone, 2-(1-hydroxy-3-pentynyl)cyclopentanone, 2-(1-hydroxyhexyl)cyclopentanone, 2-(1-hydroxyheptyl)cyclopentanone, 2-(1-hydroxyoctyl)cyclopentanone, 2-(1-hydroxy-2-methylpropyl)cyclopentanone, 2-(1-hydroxy-2-methylbutyl)cyclopentanone, 2-(1-hydroxy-2-methylpentyl)cyclopentanone, 2-(1-hydroxy-2-methylhexyl)cyclopentanone, 2-(1-hydroxy-3-methylbutyl)cyclopentanone, 2-(1-hydroxy-3-methylpentyl)cyclopentanone, 2-(1-hydroxy-3-methylhexyl)cyclopentanone, 2-(1-hydroxy-4-methylpentyl)cyclopentanone and 2-(1-hydroxy-5-methylhexyl)cyclopentanone.

In the invention, a process for producing a 2-alkylidenecyclopentanone represented by the general formula (3) which is another starting material is also not particularly limited, but as a representative process, there may be mentioned a process for producing the compound via an aldol condensation well known to those skilled in the art starting from a cyclopentanone represented by the general formula (4) and an aliphatic carbonyl compound represented by the general formula (5), for example.

Specifically, for example, an aimed 2-alkylidenecyclopentanone can be also produced by reacting a cyclopentanone represented by the general formula (4) with an aliphatic carbonyl compound represented by the general formula (5) in the presence of sodium hydroxide as a catalyst to produce a 2-(1-hydroxyalkyl)cyclopentanone and, after isolation of the product, subjecting it to dehydration. On the other hand, an aimed 2-alkylidenecyclopropanone can be directly produced by reacting a cyclopentanone represented by the general formula (4) with an aliphatic carbonyl compound represented by the general formula (5) in the presence of sodium hydroxide as a catalyst without isolation of a 2-(1-hydroxyalkyl)cyclopentanone.

At the use of a 2-alkylidenecyclopentanone thus obtained as a starting material of the invention, the reaction product can be used as it is without purification or as a product purified by distillation or the like.

In the 2-alkylidenecyclopentanone represented by the following general formula (3):

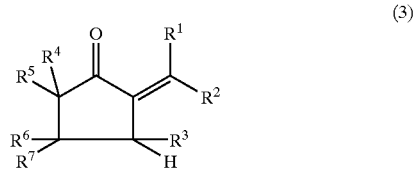

(3)

$R^1$, $R^2$, $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond.

The alkylidene group by which the above compound is substituted at the 2-position is selected from the group consisting of methylidene group, ethylidene group, propylidene group, butylidene group, pentylidene group, hexylidene group, heptylidene group, octylidene group, nonylidene group, decylidene group, 2-methylpropylidene group, 2-methylbutylidene group, 2-methylpentylidene group, 2-methylhexylidene group, 2-methyloctylidene group, 3-methylbutylidene group, 3-methylpentylidene group, 3-methylhexylidene group, 4-methylpentylidene group, 5-methylhexylidene group, 1-methylethylidene group, 1-methylpropylidene group, 1-methylbutylidene group, 1-methylpentylidene group, 1-methylhexylidene group, 1-methylheptylidene group, 1-methyloctylidene group, 1,3-dimethylbutylidene group, 1-ethylpropylidene group, and benzylidene group.

As cyclopentanones substituted at the 2-position, there may be mentioned those wherein the following cyclopentanones are substituted by any of the above alkylidene group at the 2-position. Specific examples of the cyclopentanones to be substituted include cyclopentanone, 5-methylcyclopentanone, 3- or 4-methylcyclopentanone, 5-ethylcyclopentanone, 5-propylcyclopentanone, 5-isopropylcyclopentanone, 5-butylcyclopentanone, 5-tert-butylcyclopentanone, 5-iso-butylcyclopentanone, 5-pentylcyclopentanone, 5-hexylcyclopentanone, 5-heptylcyclopentanone, 5-octylcyclopentanone, 5-decylcyclopentanone, 5,5-dimethylcyclopentanone, 4,5-dimethylcyclopentanone, 3,5-dimethylcyclopentanone, and 3,4,5-trimethylcyclopentanone.

Among cyclopentanones substituted at the 2-position, more preferred are compounds wherein $R^1$ is hydrogen atom, $R^2$, $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond.

Specifically, examples of the alkylidene group bonded to the cyclopentanones at the 2-position include methylidene group, ethylidene group, propylidene group, butylidene group, pentylidene group, hexylidene group, heptylidene group, octylidene group, nonylidene group, decylidene group, 2-methylpropylidene group, 2-methylbutylidene group, 2-methylpentylidene group, 2-methylhexylidene group, 2-methylheptylidene group, 2-methyloctylidene group, 3-methylbutylidene group, 3-methylpentylidene group, 3-methylhexylidene group, 4-methylpentylidene group and 5-methylhexylidene group.

As cyclopentanones substituted at the 2-position, there may be mentioned those wherein the following cyclopentanones are substituted by any of the above alkylidene group at the 2-position. Specific examples of the cyclopentanones to be substituted include cyclopentanone, 5-methylcyclopentanone, 3- or 4-methylcyclopentanone, 5-ethylcyclopentanone, 5-propylcyclopentanone, 5-isopropylcyclopentanone, 5-butylcyclopentanone, 5-tert-butylcyclopentanone, 5-iso-butylcyclopentanone, 5-pentylcyclopentanone, 5-hexylcyclopentanone, 5-heptylcyclopentanone, 5-octylcyclopentanone, 5-decylcyclopentanone, 5,5-dimethylcyclopentanone, 4,5-dimethylcyclopentanone, 3,5-dimethylcyclopentanone, and 3,4,5-trimethylcyclopentanone.

More preferred are compounds wherein $R^2$ is an alkyl group having 1 to 10 carbon atoms which may have any one or more substituents or an aromatic group which may have any one or more substituents, and $R^1$, $R^3$, $R^4$, $R^5$, $R^6$ and $R^7$ each is hydrogen atom.

Specific examples of the compounds include 2-ethylidenecyclopentanone, 2-propylidenecyclopentanone, 2-butylidenecyclopentanone, 2-pentylidenecyclopentanone, 2-hexylidenecyclopentanone, 2-heptylidenecyclopentanone, 2-octylidenecyclopentanone, 2-nonylidenecyclopentanone, 2-decylidenecyclopentanone, 2-(2-methylpropylidene)cyclopentanone, 2-(2-methylbutylidene)cyclopentanone, 2-(2-methylpentylidene)cyclopentanone, 2-(2-methylhexylidene)cyclopentanone, 2-(2-methyloctylidene)cyclopentanone, 2-(3-methylbutylidene)cyclopentanone, 2-(3-methylpentylidene)cyclopentanone, 2-(3-methylhexylidene)cyclopentanone, 2-(4-methylpentylidene)cyclopentanone and 2-(5-methylhexylidene)cyclopentanone.

Particularly preferred are compounds wherein $R^2$ is a linear or branched alkyl group having 2 to 8 carbon atoms which may have one or more unsaturated bonds, and $R^1$, $R^3$, $R^4$, $R^5$, $R^6$ and $R^7$ each is hydrogen atom.

Specific examples of the compounds include 2-propylidenecyclopentanone, 2-butylidenecyclopentanone, 2-pentylidenecyclopentanone, 2-hexylidenecyclopentanone, 2-heptylidenecyclopentanone, 2-octylidenecyclopentanone, 2-(2-methylpropylidene)cyclopentanone, 2-(2-methylbutylidene)cyclopentanone, 2-(2-methylpentylidene) cyclopentanone, 2-(2-methylhexylidene)cyclopentanone, 2-(3-methylbutylidene)cyclopentanone, 2-(3-methylpentylidene)cyclopentanone, 2-(3-methylhexylidene) cyclopentanone, 2-(4-methylpentylidene)cyclopentanone and 2-(5-methylhexylidene)cyclopentanone.

The 2-alkyl-2-cyclopentenone represented by the following general formula (2):

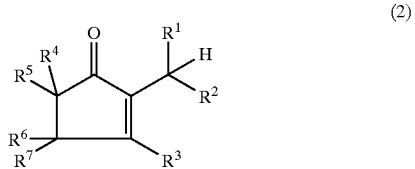

(2)

which is an aimed compound of the invention is a compound wherein $R^1$, $R^2$, $R^3$, $R^4$, $R^5$, $R^6$ and $R^7$ each independently represents hydrogen atom, an alkyl group having 1 to 10 carbon atoms which may have any one or more substituents or an aromatic group which may have any one or more substituents, and each of (1) $R^6$ or $R^7$ with $R^3$ and (2) $R^6$ or $R^7$ with $R^4$ or $R^5$ may be together combined to form a ring which may have a double bond).

In the above compound (2), examples of the alkyl group bonded to the 2-cyclopentenone at the 2-position include methyl group, ethyl group, propyl group, butyl group, pentyl group, 3-pentenyl group, 3-pentynyl group, hexyl group, heptyl group, octyl group, nonyl group, decyl group, 2-methylpropyl group, 2-methylbutyl group, 2-methylpentyl group, 2-methylhexyl group, 2-methyloctyl group, 3-methylbutyl group, 3-methylpentyl group, 3-methylhexyl group, 4-methylpentyl group, 5-methylhexyl group, 1-methylethyl group, 1-methylpropyl group, 1-methylbutyl group, 1-methylpentyl group, 1-methylhexyl group, 1-methylheptyl group, 1-methyloctyl group, 1,3-dimethylbutyl group, 1-ethylpropyl group, and phenylmethyl group.

As cyclopentanones substituted at the 2-position, there may be mentioned those wherein the following cyclopentanones are substituted by any of the above alkyl group at the 2-position. Specific examples of the 2-cyclopentenones to be substituted include 2-cyclopentenone, 5-methyl-2-cyclopentenone, 3- or 4-methyl-2-cyclopentenone, 5-ethyl-2-cyclopentenone, 5-propyl-2-cyclopentenone, 5-isopropyl-2-cyclopentenone, 5-butyl-2-cyclopentenone, 5-tert-butyl-2-cyclopentenone, 5-iso-butyl-2-cyclopentenone, 5-pentyl-2-cyclopentenone, 5-hexyl-2-cyclopentenone, 5-heptyl-2-cyclopentenone, 5-octyl-2-cyclopentenone, 5-decyl-2-cyclopentenone, 5,5-dimethyl-2-cyclopentenone, 4,5-dimethyl-2-cyclopentenone, 3,5-dimethyl-2-cyclopentenone, and 3,4,5-trimethyl-2-cyclopentenone.

Preferred are compound wherein $R^1$ is hydrogen atom, $R^2$, $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond.

In the above compound, examples of the alkyl group bonded to the 2-cyclopentenone at the 2-position include methyl group, ethyl group, propyl group, butyl group, pentyl group, 3-pentenyl group, 3-pentynyl group, hexyl group, heptyl group, octyl group, nonyl group, decyl group, 2-methylpropyl group, 2-methylbutyl group, 2-methylpentyl group, 2-methylhexyl group, 2-methyloctyl group, 3-methylbutyl group, 3-methylpentyl group, 3-methylhexyl group, 4-methylpentyl group and 5-methylhexyl group.

As 2-cyclopentenones substituted at the 2-position, there may be mentioned those wherein the following cyclopentenones are substituted by any of the above alkyl group at the 2-position. Specific examples of the 2-cyclopentenones to be substituted include 2-cyclopentenone, 5-methyl-2-cyclopentenone, 3- or 4-methyl-2-cyclopentenone, 5-ethyl-2-cyclopentenone, 5-propyl-2-cyclopentenone, 5-isopropyl-2-cyclopentenone, 5-butyl-2-cyclopentenone, 5-tert-butyl-2-cyclopentenone, 5-iso-butyl-2-cyclopentenone, 5-pentyl-2-cyclopentenone, 5-hexyl-2-cyclopentenone, 5-heptyl-2-cyclopentenone, 5-octyl-2-cyclopentenone, 5-decyl-2-cyclopentenone, 5,5-dimethyl-2-cyclopentenone, 4,5-dimethyl-2-cyclopentenone, 3,5-dimethyl-2-cyclopentenone, and 3,4,5-trimethyl-2-cyclopentenone.

More preferred are compounds wherein $R^2$ is an alkyl group having 1 to 10 carbon atoms which may have any one or more substituents or an aromatic group which may have any one or more substituents, and $R^1$, $R^3$, $R^4$, $R^5$, $R^6$ and $R^7$ each is hydrogen atom.

Specific examples of the compounds include 2-ethyl-2-cyclopentenone, 2-propyl-2-cyclopentenone, 2-butyl-2-cyclopentenone, 2-pentyl-2-cyclopentenone, 2-(3-pentenyl)-2-cyclopentenone, 2-(3-pentynyl)-2-cyclopentenone, 2-hexyl-2-cyclopentenone, 2-heptyl-2-cyclopentenone, 2-octyl-2-cyclopentenone, 2-nonyl-2-cyclopentenone, 2-decyl-2-cyclopentenone, 2-(2-methylpropyl)-2-cyclopentenone, 2-(2-methylbutyl)-2-cyclopentenone, 2-(2-methylpentyl)-2-cyclopentenone, 2-(2-methylhexyl)-2-cyclopentenone, 2-(2-methyloctyl)-2-cyclopentenone, 2-(3-methylbutyl)-2-cyclopentenone, 2-(3-methylpentyl)-2-cyclopentenone, 2-(3-methylhexyl)-2-cyclopentenone, 2-(4-methylpentyl)-2-cyclopentenone and 2-(5-methylhexyl)-2-cyclopentenone.

Particularly preferred are compounds wherein $R^2$ is a linear or branched alkyl group having 2 to 8 carbon atoms which may have one or more unsaturated bonds, and $R^1$, $R^3$, $R^4$, $R^5$, $R^6$ and $R^7$ each is hydrogen atom.

Specific examples of the compounds include 2-propyl-2-cyclopentenone, 2-butyl-2-cyclopentenone, 2-pentyl-2-cyclopentenone, 2-(3-pentenyl)-2-cyclopentenone, 2-(3-pentynyl)-2-cyclopentenone, 2-hexyl-2-cyclopentenone, 2-heptyl-2-cyclopentenone, 2-octyl-2-cyclopentenone, 2-(2-methylbutyl)-2-cyclopentenone, 2-(2-methylpentyl)-2-cyclopentenone, 2-(2-methylhexyl)-2-cyclopentenone, 2-(3-methylbutyl)-2-cyclopentenone, 2-(3-methylpentyl)-2-cyclopentenone, 2-(3-methylhexyl)-2-cyclopentenone, 2-(4-methylpentyl)-2-cyclopentenone and 2-(5-methylhexyl)-2-cyclopentenone.

One characteristic of the invention is that, in the reaction of forming a 2-alkyl-2-cyclopentenone represented by the general formula (2) by dehydration followed by isomerization of a 2-(1-hydroxyalkyl)cyclopentanone represented by the general formula (1) or by isomerization of 2-alkylidenecyclopentanone represented by the general formula (3), a bromine compound and/or an iodine compound are employed and made present in the reaction system.

The bromine compound to be used in the invention means a compound which forms bromine in the reaction system under the conditions used in the invention and the iodine compound means a compound which forms iodine in the reaction system under the conditions used in the invention.

Furthermore, the bromine compound includes bromine itself and the above iodine compound includes iodine itself.

Thus, the invention also involves, in addition to a method of adding bromine and/or iodine, a method of forming bromine and/or iodine in the reaction system and a method of forming an active species having ability almost equal to that of the active species formed at the time when bromine and/or iodine are added to the reaction system, by adding a bromine compound and/or an iodine compound to the reaction system.

The method of forming bromine and/or iodine in the reaction system and a method of forming an active species almost equal to the active species formed at the time when bromine and/or iodine are added to the reaction system are not particularly limited but the following may be exemplified:

1) hydrohalogenic acids containing bromine ion and/or iodine ion, and salts thereof,
2) organic compounds having carbon-bromine bond and/or carbon-iodine bond,
3) organic compounds having silicon-bromine bond and/or silicon-iodine bond,
4) organic compounds having nitrogen-bromine bond and/or nitrogen-iodine bond,
5) compounds having bond(s) between boron, phosphorus or sulfur and bromine and/or iodine, and
6) metal complex compounds containing bromine and/or iodine. These compounds are oxidized with an oxidizing agent such as oxygen in the air or reacted with a reaction substrate or solvent to form bromine and/or iodine.

Preferably, bromine and iodine are mentioned as specific examples but the invention is not limited thereto.

When illustrated on the basis of the reaction starting material, the amount of the above bromine compound and/or iodine compound to be used is preferably from 0.0001 to 2.0% by weight, more preferably from 0.01 to 0.5% by weight in terms of bromine and/or iodine. The larger amount of the compounds results in the faster reaction rate, but is economically disadvantageous.

The reaction temperature varies depending on the bromine compound and/or iodine compound, but generally ranges from 70 to 220° C., preferably from 100 to 170° C.

Moreover, the reaction may proceed without any solvent but it is preferred to use an appropriate amount of a solvent. As the solvent, use can be made of hydrocarbons such as toluene, xylene, decaline, tetraline, hexane, heptane, n-octane, isooctane, cyclooctane and cyclododecane, halogenated hydrocarbons such as tetrachloroethane, tetrachloroethylene and ketones such as cyclopentanone.

The amount thereof varies depending on the solvent to be used and hence is not particularly limited, but it is common to control the ratio of the volume (ml) of the solvent to the weight (g) of the reaction starting material to be 1/5 to 5/1.

According to the invention, it is enabled to produce a 2-alkyl-2-cyclopentenone represented by the general formula (2) in one step and easily in high yields. Namely, a 2-alkyl-2-cyclopentenone can be produced in one step and easily in high yields by facile operation that a bromine compound and/or an iodine compound is added to a reaction system containing a 2-(1-hydroxyalkyl)cyclopentanone represented by the general formula (1).

The following will explain the invention with reference to Examples but the invention is by no means limited thereto.

Incidentally, the instruments employed for measuring the physical properties in Examples are as follows.

Chemical Purity
  Gas chromatograph: HP-6890 (Hewlett-Packard)
  Column: HP-5 (30 m×0.25 mm×0.25 mm)
Nuclear Magnetic Resonance
  $^1$H-NMR: Bruker-AMX400 (400 MHz) (Bruker)
Mass Spectrometry (GC-MS)
  HP-6890 (Hewlett-Packard)
  Column: HP-1 (60 m×0.25 mm×0.25 mm)

REFERENCE EXAMPLE 1

Synthesis of 2-(1-hydroxypentyl)cyclopentanone

Into a 2-litter four-neck flask fitted with a thermometer, a reflux condenser and a stirrer were added sodium hydroxide (3.2 g) and water (300 ml). Then, a mixture of pentanal (86 g) and cyclopentanone (152 g) was added dropwise with stirring at 0–5° C. over a period of 2 hours. After the addition, the reaction mixture was stirred at room temperature for 1 hour to complete the reaction. Hexane (150 ml) was added to the reaction mixture and the layers were separated from each other. The resulting organic layer was washed with an aqueous solution (200 ml) of acetic acid (1 g) and then separated. The resulting organic layer was washed with saturated brine and separated. The organic layer was evaporated on a rotary evaporator under reduced pressure to recover hexane and unreacted cyclopentanone, whereby a crude product (173 g) was obtained. The product was distilled using a Claisen distillation apparatus to obtain 127 g of 2-(1-hydroxypentyl)cyclopentanone (boiling point: 115° C./933 Pa; GC purity: 95%). The remaining 5% was 2-pentylidenecyclopentanone which is a dehydration product.

REFERENCE EXAMPLE 2

Synthesis of 2-(1-hydroxyhexyl)cyclopentanone

Into a 2-litter four-neck flask fitted with a thermometer, a reflux condenser and a stirrer were added sodium hydroxide (3.2 g) and water (300 ml). Then, a mixture of hexanal (100 g) and cyclopentanone (152 g) was added dropwise thereto under stirring at 0–5° C. over a period of 2 hours. After the addition, the reaction mixture was stirred at room temperature for 1 hour to complete the reaction. Hexane (150 ml) was added to the reaction mixture and the layers were separated from each other. The resulting organic layer was washed with an aqueous solution (200 ml) of acetic acid (1 g) and then separated. The resulting organic layer was further washed with saturated brine and separated. The organic layer was evaporated on a rotary evaporator under reduced pressure to recover hexane and unreacted cyclopentanone, whereby a crude product (188 g) was obtained. The product was distilled using a Claisen distillation apparatus to obtain 142 g of 2-(1-hydroxyhexyl) cyclopentanone (boiling point: 107–108° C./666 Pa; GC purity: 94%). The remaining 6% was 2-hexylidenecyclopentanone which is a dehydration product.

REFERENCE EXAMPLE 3

Synthesis of 2-(1-hydroxyheptyl)cyclopentanone

Into a 2-litter four-neck flask fitted with a thermometer, a reflux condenser and a stirrer were added sodium hydroxide (3.2 g) and water (300 ml). Then, a mixture of heptanal (114 g) and cyclopentanone (152 g) was added dropwise thereto under stirring at 0–5° C. over a period of 2 hours. After the addition, the reaction mixture was stirred at room temperature for 1 hour to complete the reaction. Hexane (150 ml) was added to the reaction mixture and the layers were separated from each other. The resulting organic layer was washed with an aqueous solution (200 ml) of acetic acid (1 g) and separated. Then, the resulting organic layer was washed with saturated brine and separated. The organic layer was evaporated on a rotary evaporator under reduced pressure to recover hexane and unreacted cyclopentanone, whereby a product (202 g) was obtained. The product was distilled using a Claisen distillation apparatus to obtain 154 g of 2-(1-hydroxyheptyl)cyclopentanone (boiling point: 112–114° C./666 Pa; GC purity: 92%). The remaining 8% was 2-heptylidenecyclopentanone which is a dehydration product.

REFERENCE EXAMPLE 4

Synthesis of 2-pentylidenecyclopentanone

In a 300 ml four-neck flask fitted with a thermometer, a reflux condenser and a stirrer were placed 2-(1-hydroxypentyl)cyclopentanone (70 g) synthesized in Reference Example 1, oxalic acid (0.7 g) and toluene (140 ml), and the whole was refluxed to allow dehydration to proceed. The formed water was removed and the reaction was continued until water was not formed any more (about 2.5 hours). The reaction mixture was washed with water and the layers were separated from each other. The resulting organic layer was further washed with saturated brine and separated. The organic layer was evaporated on a rotary evaporator under reduced pressure to recover toluene and unreacted cyclopentanone, whereby a crude product (63 g) was obtained. The product was distilled using a Widmer distillation apparatus to obtain 52 g of 2-pentylidenecyclopentanone (boiling point: 92° C./533 Pa).

REFERENCE EXAMPLE 5

Synthesis of 2-hexylidenecyclopentanone

In a 300 ml four-neck flask fitted with a thermometer, a reflux condenser and a stirrer were placed 2-(1-hydroxyhexyl)cyclopentanone (85 g) synthesized in Reference Example 2, oxalic acid (1.0 g) and toluene (150 ml), and the whole was refluxed to allow dehydration to proceed. The formed water was removed and the reaction was continued until water was not formed any more (about 3 hours). The reaction mixture was washed with water and the layers were separated from each other. Further, the resulting organic layer was washed with saturated brine and separated. The organic layer was evaporated on a rotary evaporator under reduced pressure to recover toluene and unreacted cyclopentanone, whereby a crude product (78 g) was obtained. The product was distilled using a Claisen distillation apparatus to obtain 67 g of 2-hexylidenecyclopentanone (boiling point: 92° C./533 Pa; GC purity: 98.5%).

REFERENCE EXAMPLE 6
Synthesis of 2-heptylidenecyclopentanone

In a 300 ml four-neck flask fitted with a thermometer, a reflux condenser and a stirrer were placed 2-(1-hydroxyheptyl)cyclopentanone (70 g) synthesized in Reference Example 3, oxalic acid (0.7 g) and toluene (140 ml), and the whole was refluxed to allow dehydration to proceed. The formed water was removed and the reaction was continued until water was not formed any more (about 2.5 hours). The reaction mixture was washed with water and the layers were separated from each other. Further, the resulting organic layer was washed with saturated brine and separated. The organic layer was evaporated on a rotary evaporator under reduced pressure to recover toluene and unreacted cyclopentanone, whereby a crude product (63 g) was obtained. The product was distilled using a Claisen distillation apparatus to obtain 55 g of 2-heptylidenecyclopentanone (boiling point: 56° C./400 Pa; GC purity: 98.5%).
MS (m/e): 180 ($M^+$, 22), 123 (64), 110 (18), 97 (100), 84 (49), 67 (18), 54 (16), 43 (11).

EXAMPLE 1

Synthesis of 2-pentyl-2-cyclopentenone

In a 100 ml four-neck flask fitted with a thermometer, a reflux condenser and a stirrer were placed 2-(1-hydroxypentyl)cyclopentanone (20 g) synthesized in Reference Example 1, iodine (0.01 g) and xylene (10 ml), and water was removed under refluxing, followed by 2 hours of the reaction at 170° C. The reaction mixture was washed with water and the layers were separated from each other. Further, the resulting organic layer was washed with saturated brine and separated. The organic layer was evaporated on a rotary evaporator under reduced pressure to recover xylene, whereby a crude product (19.8 g) was obtained. The product was distilled using a Claisen distillation apparatus to obtain 17.4 g of 2-pentyl-2-cyclopentenone (boiling point: 105° C./933 Pa; GC purity: 98.2%).

EXAMPLE 2

Synthesis of 2-pentyl-2-cyclopentenone

In a 50 ml four-neck flask fitted with a thermometer, a reflux condenser and a stirrer were placed 2-(1-hydroxypentyl)cyclopentanone (20 g) synthesized in Reference Example 1, N-iodosuccinimide (0.1 g) and toluene (10 ml), and water was removed under refluxing, followed by 4 hours of the reaction at 150° C. The reaction mixture was washed with water and the layers were separated from each other. Further, the resulting organic layer was washed with saturated brine and separated. The organic layer was evaporated on a rotary evaporator under reduced pressure to recover toluene, whereby a crude product was obtained. The product was distilled using a Claisen distillation apparatus to obtain 15.3 g of 2-pentyl-2-cyclopentenone (boiling point: 104° C./930 Pa; GC purity: 98.4%).

EXAMPLE 3

Synthesis of 2-heptyl-2-cyclopentenone

In a 100 ml four-neck flask fitted with a thermometer, a reflux condenser and a stirrer were placed 2-(1-hydroxyheptyl)cyclopentanone (40 g) synthesized in Reference Example 3, bromine (0.4 g) and n-octane (10 ml), and water was removed under refluxing, followed by 4 hours of the reaction at 120° C. The reaction mixture was washed with water and the layers were separated from each other. The resulting organic layer was washed with saturated brine and separated. The organic layer was evaporated on a rotary evaporator under reduced pressure to recover n-octane, whereby a crude product (39 g) was obtained. The product was distilled using a Claisen distillation apparatus to obtain 32 g of 2-heptyl-2-cyclopentenone (boiling point: 111° C./900 Pa; GC purity: 97.8%).

EXAMPLE 4

Synthesis of 2-hexyl-2-cyclopentenone

In a 30 ml four-neck flask fitted with a thermometer, a reflux condenser and a stirrer were placed 2-(1- hydroxyhexyl)cyclopentanone (20 g) synthesized in Reference Example 2 and iodine (5 mg), followed by 6 hours of the reaction at 150° C. The crude product was purified by column chromatography (hexane/ethyl acetate: 95/5) to obtain 15.3 g of 2-hexyl-2-cyclopentenone (GC purity: 99.1%).

EXAMPLE 5

Synthesis of 2-hexyl-2-cyclopentenone

In a 50 ml three-neck flask fitted with a thermometer, a condenser and a stirrer were placed 2-hexylidenecyclopentanone (15 g) synthesized in Reference Example 5 and bromine (0.03 g), followed by 6 hours of the reaction at 100–120° C. The crude product was purified by column chromatography (hexane/ethyl acetate: 95/5) to obtain 12.5 g of 2-hexyl-2-cyclopentenone (GC purity: 98.5%).

EXAMPLE 6

Synthesis of 2-pentyl-2-cyclopentenone

In a 100 ml four-neck flask fitted with a thermometer, a reflux condenser and a stirrer were placed 2-pentylidenecyclopentanone (30 g) synthesized in Reference Example 4, cyclopentanone (31.6 ml) and iodine (30 mg), followed by 4 hours of the reaction under refluxing. The reaction mixture was washed with water and the layers were separated from each other. The resulting organic layer was washed with saturated brine and separated. The organic layer was evaporated on a rotary evaporator under reduced pressure to recover cyclopentanone, whereby a crude product (30.2 g) was obtained. The product was distilled using a Claisen distillation apparatus to obtain 25.3 g of 2-pentyl-2-cyclopentenone (boiling point: 101° C./900 Pa; GC purity: 97.9%).

EXAMPLE 7

Synthesis of 2-heptyl-2-cyclopentenone

In a 100 ml four-neck flask fitted with a thermometer, a reflux condenser and a stirrer were placed 2-heptylidenecyclopentanone (20 g) synthesized in Reference Example 6, bromine (0.05 g) and tetrachloroethylene (10 ml), followed by 4 hours of the reaction under refluxing. The reaction mixture was washed with water and the layers were separated from each other. Further, the resulting organic layer was washed with saturated brine and separated. The organic layer was evaporated on a rotary evaporator under reduced pressure to recover tetrachloroethylene, whereby a crude product (19 g) was obtained. The product was distilled using a Claisen distillation apparatus to obtain 16.8 g of 2-heptyl-2-cyclopentenone (boiling point: 111° C./900 Pa; GC purity: 97.3%).

EXAMPLE 8

Synthesis of 2-pentyl-2-cyclopentenone

In a 100 ml four-neck flask fitted with a thermometer, a reflux condenser and a stirrer were placed 2-pentylidenecyclopentanone (50 g) synthesized in Reference Example 4 and iodine (5 mg), followed by 3 hours of the reaction at 180° C. The crude product (50 g) was distilled without any treatment using a Claisen distillation apparatus to obtain 39 g of 2-pentyl-2-cyclopentenone (boiling point: 105° C./933 Pa; GC purity: 98.3%).

While the invention has been described in detail and with reference to specific embodiments thereof, it will be apparent to one skilled in the art that various changes and modifications can be made therein without departing from the scope thereof.

This application is based on Japanese patent application No. 2001-366023 filed Nov. 30, 2001, the entire contents thereof being hereby incorporated by reference.

What is claimed is:

1. A process for producing a 2-alkyl-2-cyclopentenone represented by the following general formula (2):

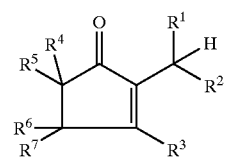

(2)

(wherein $R^1$, $R^2$, $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond), which comprises a step of dehydrative isomerization of a 2-(1-hydroxyalkyl)cyclopentanone represented by the following general formula (1):

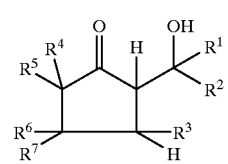

(1)

(wherein $R^1$, $R^2$, $R^3$, $R^4$, $R^5$, $R^6$ and $R^7$ are the same as above)

in the presence of a bromine compound and/or an iodine compound, wherein the amount of the bromine compound or iodine compound is from 0.0001 to 2.0% by weight in terms of bromine or iodine relative 2-(1-hydroxyalkyl) cyclopentanone represented by the formula (1).

2. The process for producing a 2-alkyl-2-cyclopentenone according to claim 1, wherein $R^1$ in the general formula (1) is hydrogen atom.

3. The process for producing a 2-alkyl-2-cyclopentenone according to claim 1, wherein $R^3$, $R^4$, $R^5$, $R^6$ and $R^7$ in the general formula (1) are each hydrogen atom.

4. The process for producing a 2-alkyl-2-cyclopentenone according to claim 1, wherein, in the general formula (1), $R^2$ is a linear or branched alkyl group having 2 to 8 carbon atoms which may have one or more unsaturated bonds.

5. A process for producing a 2-alkyl-2-cyclopentenone represented by the following general formula (2):

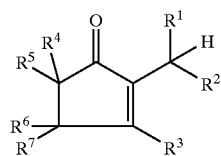 (2)

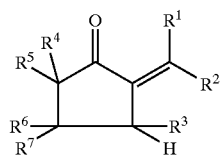 (3)

(wherein $R^1$, $R^2$, $R^3$, $R^4$, $R^5$, $R^6$ and $R^7$ each independently represents hydrogen atom, an alkyl group having 1 to 10 carbon atoms which may have one or more substituents or an aromatic group which may have one or more substituents, and each of (1) $R^6$ or $R^7$ with $R^3$ and (2) $R^6$ or $R^7$ with $R^4$ or $R^5$ may be together combined to form a ring which may have a double bond), which comprises a step of isomerization of a 2-alkylidenecyclopentanone represented by the following general formula (3):

(wherein $R^1$, $R^2$, $R^3$, $R^4$, $R^5$, $R^6$ and $R^7$ are the same as above)

in the presence of a bromine compound and/or an iodine compound, wherein the amount of the bromine compound or iodine compound is from 0.0001 to 2.0% by weight in terms of bromine or iodine relative to 2-alkylidenecyclopentanone represented by the formula (3).

* * * * *